United States Patent [19]

Becker

[11] 4,237,005
[45] Dec. 2, 1980

[54] METHOD OF BREAKING OIL-IN-WATER EMULSIONS

[75] Inventor: Larry W. Becker, Wilmington, Del.

[73] Assignee: Betz Laboratories, Inc., Trevose, Pa.

[21] Appl. No.: 45,544

[22] Filed: Jun. 4, 1979

Related U.S. Application Data

[62] Division of Ser. No. 941,537, Sep. 11, 1978, Pat. No. 4,190,615.

[30] Foreign Application Priority Data

Mar. 28, 1979 [CA] Canada .................... 324395

[51] Int. Cl.$^3$ .............................. B01D 17/04
[52] U.S. Cl. ...................... 210/708; 210/729; 252/340; 252/345; 252/358
[58] Field of Search ............... 252/340, 345, 358; 210/54 A, 43

[56] References Cited

U.S. PATENT DOCUMENTS

| | | | |
|---|---|---|---|
| 1,596,593 | 8/1926 | De Groote | 252/340 |
| 3,033,889 | 5/1962 | Chiddix et al. | 252/345 X |
| 3,214,454 | 10/1965 | Blaser et al. | 260/502.4 A X |
| 3,387,024 | 6/1968 | Quimby | 260/439 R X |
| 3,400,151 | 9/1968 | Quimby et al. | 260/439 R X |
| 3,621,081 | 11/1971 | Prentice | 260/924 |

Primary Examiner—Richard D. Lovering
Attorney, Agent, or Firm—Alexander D. Ricci; Steven H. Markowitz

[57] ABSTRACT

The use as oil-in-water emulsion breakers of phosphonic acid ester condensate oligomers is disclosed which oligomers are ester condensates of alkyl-1-hydroxy-1,1-diphosphonic acid having the formula:

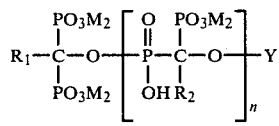

where $R_1$ and $R_2$ each represent a group having the formula $C_xH_{2x+1}$, where x is from 6 to 13; Y is

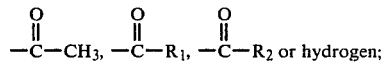

M is a water soluble cation such as Na, K or $NH_4$, and n is 1 or greater.

7 Claims, No Drawings

METHOD OF BREAKING OIL-IN-WATER EMULSIONS

This is a division of application Ser. No. 941,537 filed Sept. 11, 1978, now U.S. Pat. No. 4,190,615, issued Feb. 26, 1980; and the parent application is incorporated herein by reference.

The present invention relates to the use as reverse emulsion breakers of a new series of organophosphorous compounds which are oligomeric ester condensates of alkyl-1-hydroxy-1,1-diphosphonic acid having as an end group a $C_6$–$C_{13}$ alkyl group.

BACKGROUND ART

Condensates of ethane-1-hydroxy-1,1-diphosphonic acid are known such as those described in U.S. Pat. Nos. 3,387,024; 3,400,151 and 3,621,081. In the first two noted patents, the condensates are limited to dimers of ethane-1-hydroxy-1,1-diphosphonates joined by C—O—C bonds or P—O—P bonds, as opposed to the oligomeric ester compounds of the present invention which contain C—O—P bonds. While the latter mentioned patent, U.S. Pat. No. 3,621,081, to Prentice does disclose oligomeric ester compounds of phosphorous acid which contain C—O—P bonds, the patent specifically limits the compounds to those containing a methyl end group. Not only were the preparatory methods of Prentice found to be unsuitable for preparation of the $C_6$–$C_{13}$ compounds of the present invention, but the higher homologs were unexpectedly found to possess "reverse" emulsion breaking properties not found in the Prentice oligomer. Accordingly, the present invention relates to the use of these compounds as "reverse" emulsion breakers.

DISCLOSURE OF THE INVENTION

The phosphonic acid ester condensate oligomers to which the present invention pertain have the general formula

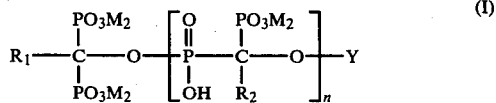

where $R_1$ and $R_2$ each represent a group but not necessarily the same group having the formula $C_xH_{2x+1}$, where x is from 6 up to and including 13; Y is

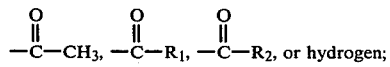

M is a water soluble cation such as Na, K or $NH_4$; and where n is 1 or greater so long as the oligomer is water soluble. It is preferred that n have a value of from 1 to about 16. For $R_1$ and $R_2$ as defined above, x is preferably 7 up to 13 and, most preferably, from 7 to 11.

The oligomers according to the present invention are prepared by:

(1) adding an excess amount of acetic anhydride to the appropriate substituted 1-hydroxy-1,1-diphosphonic acid, (2) continuing the reaction until it is substantially complete, and (3) separating the reaction product from the remaining reaction mixture.

As will become apparent from the examples below, this method of preparation is considered to be useful for preparing organo-phosphorous compounds in general which are oligomeric ester condensates of a substituted 1-hydroxy-1,1-diphosphonic acid and offers many advantages over the prior art method disclosed by Prentice.

The substituted 1-hydroxy-1,1-diphosphonic acid in preparation step (1) is represented by the general formula:

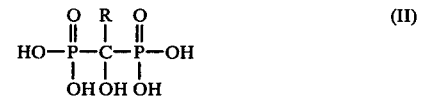

wherein R denotes an alkyl radical having 1 to 13, and preferably 3 to 13 (7 to 13 is most preferred), carbon atoms. These compounds and various methods for their perparation are well known in the art as evidenced by U.S. Pat. No. 3,214,454 to Blaser which is incorporated herein by reference. According to Blaser, these products can be produced, for example, by reacting phosphorous acid with acid chlorides or by reacting phosphorous trichloride with one of the carboxylic acids themselves. The reactions are opportunely carried out at elevated temperatures, preferably between 50° and 200° C.

Examples of compounds of Formula II are hydroxyheptane-, hydroxyoctane-, hydroxydecane-, and hydroxydodecane-1,1-diphosphonic acids.

With reference again to step (1) of the above-noted method for preparing the oligomer, it has been stated above that acetic anhydride is added to the "appropriate" substituted 1-hydroxy-1, 1-diphosphonic acid. The selection of the "appropriate" material is seen to be well within the skill of the art and would be achieved, for example, by properly matching the R group in Formula II with $R_1$ in Formula I. For example, if an oligomer of Formula I is to be made in which $R_1$ is heptyl, hydroxyoctane-1,1-diphosphonic acid is used in step (1).

To assure that an excess of acetic anhydride is added to the substituted 1-hydroxy-1,1-diphosphonic acid, the mole ratio of acetic anhydride to the latter compound is preferably from about 2:1 to about 5:1.

The reaction temperature is in the range of about 50 to 200° C. If the production of the substituted 1-hydroxy-1,1-diphosphonic acid is included as part of the overall oligomerization process (as opposed to using the material already made), the compound will already be present at this elevated temperature which is required both to initiate the oligomerization and to increase the yield of oligomer by driving the reaction to completion. A preferred temperature range is about 100° to about 180° C.

Once the oligomerization reaction is initiated by adding the excess acetic anhydride to the substituted 1-hydroxy-1,1-diphosphonic acid, the reaction is continued until it is substantially complete. Depending on the particular alkyl radical present in the 1-hydroxy-1,1-diphosphonic acid reactant the final reaction product can take the form of a crunchy solid, an oily mass, or a solution. Of course, if an oily mass or crunchy solid is formed, the "substantial completion" of the reaction is readily detected. If after several hours of reaction time, no oily mass or solid is visible, it is to be assumed that the reaction product is in the form of a solution. The reaction could take as little as about 0.5 hours or as long as about 72 hours to go substantially to completion. However, about 1 to 4 hours is considered to be suitable time for the reaction to be continued.

In the instance that the reaction product takes the form of a crunchy solid, the solid can be directly separated from the remaining reaction mixture by any well known means, such as filtration.

In the event the reaction product takes the form of an oily mass, the mass should be cooled to about 0° to 25° C. If, as a result of cooling, a solid is formed, the product can be removed from the remaining reaction mixture by filtration. If the cooling step fails to provide a readily separable product, the product can be removed by evaporation of the remaining reaction mixture; or the supernatant can be decanted and replaced with fresh acetic anhydride. The decanting step is used to remove unreacted starting materials and acetic acid which was generated from the anhydride, since these materials tend to solubilize the reaction product. If, upon addition of the fresh acetic anhydride, a solid is formed, then separation of the product by filtration can be performed; whereas, if an oily mass persists, evaporation of the remaining reaction mixture must be resorted to.

If the reaction product takes the form of a solution, a recovery method similar to that for the oily mass is followed. First, the solution is cooled to about 0° to 25° C. If a solid is formed, then separation by filtration can be used; however, if an oily mass is formed, either evaporation or the use of fresh acetic anhydride must be resorted to as discussed above.

According to the above-discussed Prentice patent, the oligomeric ester chain of ethane-1-hydroxy-1,1-diphosphonic acid (this would correspond to $R_1$ and $R_2=CH_3$ in Formula I above) is prepared by reacting an excess of the appropriate anhydride, acetic anhydride, with phosphorous acid. According to that patent, the oligomeric ester chain condensate formed by the reaction is insoluble in the acetic anhydride and readily precipitates out of solution enhancing recovery of the product. When the present inventor attempted to utilize this method for preparing the oligomers of Formula I, where $R_1$ was greater than $C_2H_5$, by reacting phosphorous acid with the appropriate higher anhydrides, the Prentice method proved to be unsuitable for the purpose. It was observed that as the alkyl groups of the anhydride increased in the number of carbon atoms, the reaction products became more oil soluble and, therefore, soluble in the anhydride. As the product became soluble in the anhydride, it became extremely difficult to separate. In fact, the present inventor was unable to obtain any solid from the reaction mixture using the Prentice method. In contradistinction to the Prentice method, the present method permits easy recovery of the product. Another problem with the Prentice method is that as the alkyl groups of the anhydrides increase about $CH_3$—, they become either very expensive or commercially unavailable.

In oil field applications, the major use of reverse emulsion breakers is at those areas where secondary oil recovery methods are being used. According to these methods, water, steam, air, fire, etc. are all used to liberate trapped oil from its geologic formation. The oil is then recovered as an oil-in-water emulsion. The recovered oil is then delivered to a physical separator or "knock-out." Free oil is removed from the separator and fed to other treatment areas. Without chemical treatment, a layer would remain in the separator as an emulsion. Chemical treatment causes the emulsion to become unstable and "break," that is separate into separate oil and water layers.

In secondary oil fields, the use of reverse emulsion breakers can also be found at those areas where slop oil is recovered and at water treatment facilities for further water cleanup prior to its reuse. Slop oils are those fractions which are inadvertently released from the wells, valves, pipes, etc., then collected and retained at a storage area for eventual oil recovery.

Of course, applications for reverse emulsion breakers are not limited to oil production fields. Other industrial applications would include, but are not necessarily limited to, oil removal at waste treatment facilities and from process waters and oil recovery in machining operations.

As a reverse emulsion breaker, the oligomer is fed as an aqueous solution. The amount of oligomer in the aqueous solution can vary over a wide range. In fact, the lower limit would only be determined by restrictions on the volume of aqueous solution required to do a given job. Accordingly, about 0.01% by weight of oligomer in the aqueous solution is considered to be the lower limit, with about 1% being the preferred lower limit. The upper limit would depend only on the amount of oligomer that could be dissolved in the aqueous medium. It is the present inventor's estimate that as high as an 85% aqueous solution (by weight) could be attained. The preferred upper limit would be about a 35% solution.

The amount of treatment can vary over a wide range and, as is well known in the art, would depend on the particular problem to be treated. Based on experience, the lower limit could be as low as about 1 part of treatment (actives basis) per million parts of oil-in-water emulsion to be treated, with the preferred lower limit being about 10 parts per million. The upper limit would be about 250 parts of active treatment per million parts of emulsion to be treated, with the preferred upper limit being about 100 parts per million.

The preparation of oligomeric ester chain condensates according to the present invention is exemplified in Examples 1-4 below.

EXAMPLE 1

In this example the phosphorous acid ester condensate oligomer of 1-hydroxyheptane-1,1-diphosphonic acid was prepared as follows:

Heptanoic acid (97.6 g; 0.75 mole) and water (13.0 g; 0.75 mole) were mixed, followed by slow addition of phosphorous trichloride (68.5 g; 0.5 mole). Although initially exothermic, the reaction becomes endothermic with the evolution of HCl. As a result, the mixture was slowly heated to 145° C. where a thick one-phase system was formed. After one hour, 250 ml of acetic anhydride were added. A gummy solid formed within 15 minutes. After one hour, the mixture was cooled to 0° C., the mother liquor was decanted and replaced with a fresh aliquot of anhydride. After standing overnight, the mixture was again cooled to 0° C., excess anhydride was decanted and the residue was dried in vacuo to give 33.4 g of a tan product corresponding to formula I where $R_1$ and $R_2$ were —$C_6H_{13}$, and Y was H,

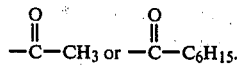

EXAMPLE 2

In this example the phosphorous acid ester condensate oligomer of 1-hydroxyoctane-1,1-diphosphonic acid was prepared as follows:

Octanoyl chloride (162 g; 1.0 mole) and phosphorous acid (82 g; 1.0 mole) were stirred and heated together to 145°–150° C. At this temperature, foaming was prevalent and boilover occurred. Accordingly, stirring was stopped to avoid boilover. The reaction mixture was then heated at 145° C. for 3 hours, cooled, and 250 cc of acetic anhydride were added. After about 1 hour the reaction mixture was cooled to 10° C., at which point a solid mass formed. The liquid was decanted and 200 ml of fresh acetic anhydride were added. The liquid was again decanted and the residue dried in vacuo to give 60 grams of product corresponding to Formula I where $R_1$ and $R_2$ were $-C_7H_{15}$, and Y was

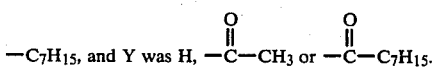

EXAMPLE 3

In this example the phosphorous acid ester condensate oligomer of 1-hydroxydecane-1,1-diphosphonic acid was prepared as follows:

Decanoyl chloride (60 g; 0.31 mole) and phosphorous acid (25.8 g; 0.31 mole) were heated with stirring to 150° C., where the two phases were miscible, and after a few minutes at 160° C., the mixture became thick, cloudy and exothermed to 180° C. Heating at 150° F. was then continued for 3 hours, at which point 200 ml of acetic anhydride were added. When the resulting reaction mixture was cooled an oily product appeared. An additional 100 ml of acetic anhydride was added causing a thick viscous oil to separate. The mixture was then cooled to 0° C., the liquid was decanted, and fresh acetic anhydride was added. After standing overnight the mixture was cooled to 10° C. and the liquid was again decanted. The residue was dried in vacuo to yield 32.8 g of product corresponding to Formula I where $R_1$ and $R_2$ were $-C_9H_{19}$ and Y was H,

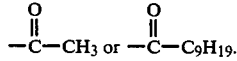

EXAMPLE 4

In this example the phosphorous acid ester condensate oligomer of 1-hydroxydodecane-1,1-diphosphonic acid was prepared as follows:

Lauroyl chloride (109.4 g; 0.5 mole) and phsophorous acid (41 g; 0.5 mole) were slowly heated with stirring to 170° C., at which point the mixture became thick with bubbling. After 15 minutes the bubbling stopped. Heating was continued at 160°–175° C. for 2 hours. The clear melt was poured into 200 ml of acetic anhydride and the temperature of the mixture was allowed to drop to room temperature. The mixture was then cooled to 10° C., but no separable product was formed. An additional 150 ml of acetic anhydride caused a precipitate to form.

The liquid was decanted from the mixture and replaced with fresh acetic anhydride, and the mixture was allowed to warm to room temperature. After standing for 24 hours, a solid mass settled to the bottom of the flask. The liquid was then decanted and the mass was dried in vacuo to yield 68.4 grams of product corresponding to Formula I where $R_1$ and $R_2$ were $-C_{11}H_{23}$ and Y was

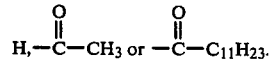

EXAMPLE 5

Several oligomeric materials corresponding to Formula I were tested for reverse emulsion breaking efficacy using oil samples from four different secondary oil production fields. The specific materials tested were those where $R_1$ and $R_2$ were $-CH_3$ (OP-1), $-C_3H_7$ (OP-3), $-C_7H_{15}$ (OP-7) and $-C_9H_{19}$ (OP-9); and 10% aqueous solutions were used.

The tests were conducted according to a testing procedure as follows:

1. the treatments were each added to a separate bottle using a microliter pipet;
2. the quantity added was such to correspond to 1, 5 and 10 ppm active material in 100 ml of solution;
3. a sample of untreated oil field emulsion was then added to each bottle;
4. each bottle was filled to 100 ml with emulsion;
5. each bottle was then capped and shaken vigorously by hand for a total of 100 shakes;
6. each bottle was then allowed to stand; and
7. visual observation was made of each solution, with any "break" of oil therefrom being noted.

The results of these tests are reported below in Table I wherein the different oil emulsion samples are simply labelled numerically as 1–4. In any instance in which a break was observed, this is indicated in the table as the dosage at which the break occurred.

TABLE I

| | TESTS FOR REVERSE EMULSION BREAKING EFFICACY | | | |
|---|---|---|---|---|
| | Oil Sample Number | | | |
| Product | (1) | (2) | (3) | (4) |
| OP-1 | None | None | None | None |
| OP-3 | None | None | None | None |
| OP-7 | None | 10 ppm | 10 ppm | None |
| OP-9 | None | 10 ppm | 10 ppm | — |

As can be seen from the results in Table I, while the lower $C_1$ and $C_3$ homologs failed to demonstrate any such efficacy, the $C_7$ and $C_9$ materials demonstrated efficacy as reverse emulsion breakers.

Having thus described my invention, I claim:

1. A method of breaking an oil-in-water emulsion comprising adding thereto an effective amount for the purpose of an aqueous solution of effective oligomeric phosphonate having the structural formula:

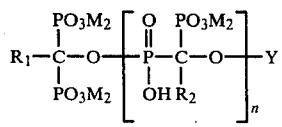

where $R_1$ and $R_2$ each represent a group having the formula $C_xH_{2x+1}$; x is from 6 up to and including 13; Y is

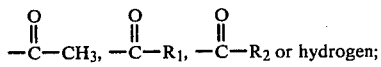

M is a water soluble cation; and n is 1 or greater so long as the oligomeric phosphonate is water soluble.

2. A method according to claim 1, wherein n is from about 1 to about 16.

3. A method according to claim 2, wherein M is selected from the group consisting of hydrogen, sodium, potassium, and ammonium.

4. A method according to claim 3, wherein x is 7 up to and including 11.

5. A method according to claim 2, wherein the phosphonate is added in an amount of from about 5 to about 150 parts per million parts of oil-in-water emulsion.

6. A method according to claim 2, wherein the oil-in-water emulsion is part of a secondary oil recovery system.

7. A method according to claim 2, wherein the oil-in-water emulsion is industrial oil-containing wastewater.

* * * * *